(12) United States Patent  (10) Patent No.: US 8,325,338 B1
Pope et al.  (45) Date of Patent: Dec. 4, 2012

(54) DETECTION OF AIRCRAFT ICING

(75) Inventors: John Pope, Laramie, WY (US); Daniel Buttry, Tempe, AZ (US); Arthur R. Toews, Laramie, WY (US)

(73) Assignee: The Blue Sky Group, Laramie, WY (US)

( * ) Notice: Subject to any disclaimer, the term of this patent is extended or adjusted under 35 U.S.C. 154(b) by 243 days.

(21) Appl. No.: 12/686,755

(22) Filed: Jan. 13, 2010

Related U.S. Application Data

(60) Provisional application No. 61/230,742, filed on Aug. 2, 2009.

(51) Int. Cl.
*G01J 3/30* (2006.01)
(52) U.S. Cl. ......................................... 356/301; 340/962
(58) Field of Classification Search .................. 356/301, 356/445, 630; 73/170.17, 170.21, 170.26; 340/962; 244/134 F
See application file for complete search history.

(56) References Cited

U.S. PATENT DOCUMENTS

| | | | | | |
|---|---|---|---|---|---|
| 5,500,530 | A | * | 3/1996 | Gregoris | 250/339.11 |
| 5,748,091 | A | * | 5/1998 | Kim | 340/583 |
| 5,841,538 | A | * | 11/1998 | Schoeffler et al. | 356/369 |
| 5,929,443 | A | * | 7/1999 | Alfano et al. | 250/341.3 |
| 6,091,335 | A | * | 7/2000 | Breda et al. | 340/580 |
| 6,819,265 | B2 | * | 11/2004 | Jamieson et al. | 340/962 |
| 7,265,846 | B2 | * | 9/2007 | Forsyth | 356/445 |
| 7,324,001 | B2 | * | 1/2008 | Crisman | 340/580 |

* cited by examiner

*Primary Examiner* — Layla Lauchman
(74) *Attorney, Agent, or Firm* — David McEwing

(57) ABSTRACT

There is disclosed a system comprising Raman spectroscopy used to detect key characteristics of ice formation on aircraft wings and engines in real time. This disclosure provides a method and apparatus for early detection of icing. The disclosed apparatus is suitable for use in aircraft, boats, oil rigs, wind turbines, and the like.

20 Claims, 12 Drawing Sheets

DETECTION OF AIRCRAFT ICING

CROSS REFERENCE TO RELATED APPLICATION

This patent application claims priority to U.S. provisional patent application 61/230,742 filed 2 Aug. 2009 which claims priority to U.S. provisional patent application 61/119,711 filed 3 Dec. 2008.

TECHNICAL FIELD

Raman spectroscopy is used to detect key characteristics of ice formation on aircraft wings and engines in real time. This disclosure provides a method and apparatus for early detection of icing. It is suitable for use in aircraft, boats, oil rigs, wind turbines, and the like.

BACKGROUND

Atmospheric icing occurs on aircraft when flying through supercooled water. When aircraft contact such supercooled water, phase transition of the water to ice occurs. Typically, icing occurs between 0° C. and −20° C. At temperatures higher than this range, water is not supercooled. At temperatures lower than this range, water usually exists in the atmosphere as ice.

There are two kinds of ice that commonly form on aircraft, glaze ice and rime ice. Glaze ice forms at warmer outside air temperatures just below 0° C. Glaze ice is a hard ice that can cause engine damage if shed in large pieces. It is also dense and heavy and can affect aircraft lift. Rime ice occurs at lower temperatures and is porous and brittle, with less chance of engine damage if shed. Rime ice is typically less dense and does not commonly affect aircraft lift. In addition, there is "Glime ice" that is a mix of rime ice and glaze ice, formed during transition temperatures between rime ice and glaze ice.

Icing conditions require atmospheric water content, generally a function of ground temperature, altitude and the type of cloud formed through which the aircraft is flying. FIG. 1 herein shows a bell curve of icing conditions as a function of temperature, altitude and droplet diameter and atmospheric water content.

In-flight icing forms when an aircraft flies through a cloud of super-cooled precipitation. As the aircraft flies, it causes the portion of the air that it encounters to move around it rapidly. Water droplets resident in that air cannot move rapidly enough, due to their mass, to avoid the aircraft and instead strike or impinge the aircraft surfaces. When such water droplets are supercooled, they change phases to solid when they strike or impinge the aircraft surfaces. Ice therefore forms on the leading or forward-facing edges of the wings, tail, antennas, windshield, radome, engine inlet, and so forth.

A dangerous way that ice acts on an aircraft is through its effect on the aerodynamics, which results in degraded performance and control. Small amounts of ice or frost add roughness to the airplane surfaces. The roughness increases the friction of the air over the surface; this is called skin friction. Large accretions can drastically alter the shape of the wing. Then, in addition to skin friction, flow separation results in a further reduction in aerodynamic performance of the aircraft. Large accretions can also cause increased weight of the aircraft, further degrading flight performance.

Aircraft control can be seriously affected by ice accretion. Ice accretion on the tail can lead to reduced elevator effectiveness, reducing the longitudinal control (nose up and down) of the aircraft. In some situations, the tail can stall or lose lift prematurely, resulting in the aircraft pitching nose down. Similarly, ice on the wing ahead of the aileron can result in roll upset. Both tail stall and roll upset are thought to be the cause of recent aircraft icing accidents.

Large aircraft and many light aircraft are equipped with in-flight ice protection systems to reduce the effect of ice. Ice protection systems are classified as de-ice or anti-ice systems. De-ice systems allow some ice to accrete, and then they periodically remove the ice. Anti-ice systems prevent ice from forming either by heating the surface above 0° C. (32° F.) or through the use of freezing-point depressants.

When aircraft encounter supercooled atmospheric water, and ice forms on wings and engines, aircraft can experience loss of lift due to weight gain and can be subject to changes in aerodynamics. When ice that has formed on an engine intake manifold or cowling fractures and breaks free, it can enter the engine and cause catastrophic mechanical damage.

If icing conditions are known to exist, or if icing begins to occur, pilots can sometimes take navigational action to avoid serious consequences. Therefore, in order for pilots to be warned of icing as soon as possible, there is a need for a system that (1) detects conditions favorable to icing, (2) detects the presence of ice, and (3) measures the rate of icing accretion. The present disclosure addresses the foregoing needs.

For aircraft application, in-flight ice detection is limited to in situ sensors, such as the mechanical Ice Detector by Rosemount Aerospace which is mounted on an aircraft surface to sense a collection of ice on a vibrating element. This sensor saturates quickly and requires heating to return to its initial state. It is also intrusive and therefore not suitable for certain aircraft environments and surfaces. A ground-based ice detection system, known as the IceHawk system by Sensor Systems Division of Goodrich Corporation, detects accreted ice on the surface of an aircraft visually by laser polarization scanning techniques. Neither system can predict ice accretion prior to the formation on the aircraft surface or before the aircraft enters an icing region of airspace during flight.

Similar temperature and relative humidity measurements are performed by interrogating atmospheric nitrogen gas and water vapor with Raman LIDAR devices. However, such devices require expensive hardware and are configured for measurements that, while stand-off, are 400 m to 3 km away from the Raman systems. Thus, such devices are not suitable for direct transfer to an engine inlet environment. Alternately, standard Raman spectrometers are used to measure types of condensed phase materials, but are not used to measure gas phase materials due to poor sensitivity of such spectrometers.

Accordingly, it is desirable to have a warning system small enough in size to be mountable on-board an aircraft and powered thereby and which has the capability of in-flight monitoring the aircraft for conditions likely to cause ice accretion on the surface of the aircraft and warn the pilot and crew of such an impending condition in sufficient time to change the heading of the aircraft. Therefore, there is a need in the art for such a system to provide sufficient flexibility that it can be deployed in a plurality of sensor response and physical configurations so that it can be used in a wide variety of applications for aircraft and other structures. There is a further need in the art for such a warning system to contain a robust set of features that enable it to maintain its sensitivity and calibration under harsh temperature, pressure and vibration conditions, to return its sensitivity after an icing event has occurred to a state that can indicate new icing events, to provide information regarding the type of ice that forms on the aircraft, and to operate effectively under a wide variety of flight conditions. The present disclosure is made to address the foregoing needs.

SUMMARY

The present disclosure provides an aircraft icing detection system for an aircraft, having a fuselage and one or a plurality of engines and wings, each having surfaces interacting with surrounding air, comprising:

(a) a Raman sensor communicating with a computer, operator, or pilot;

(b) a light train for transmitting incident radiation to aircraft surfaces or to samples of surrounding air; and (c) a light train for returning radiation scattered from the aircraft surfaces or the surrounding air and communicating with the Raman sensor.

The present disclosure further provides an aircraft icing detection system, comprising:

(a) a Raman spectrometer sensor having a plurality of input ports and communicating with a computer to calculate vibrational changes at a plurality of aircraft locations;

(b) a plurality of fiber optic lines, each having a first and a second end, wherein the first end optically communicates with an input port of a Raman sensor, and the second end is focused on a structure located on an aircraft surface.

Preferably, the Raman sensor and computer calculate vibrational changes at a plurality of aircraft locations. Preferably, the Raman spectrometer is located in the fuselage of the aircraft. Preferably, there are at least twenty fiber optic lines, each leading to various positions on the aircraft that tend to ice, including, but not limited to, forward wing edges, air speed sensors and the engine inlets.

The present disclosure provides a process for detecting a molecular monolayer or greater amounts of ice formed on an aircraft surface, comprising:

(a) providing an aircraft with a Raman sensor located in the fuselage having a plurality of input ports and communicating with a computer to calculate vibrational changes, and a plurality of fiber optic lines, each having a first and a second end, wherein the first end optically communicates with an input port of a Raman sensor, and the second end is focused on a structure located on a wing surface or an engine surface; and (b) reading each fiber optic line to detect ice formed on the surface.

Preferably, the Raman spectrometer focuses an exciting laser beam onto the surface of the structure of interest, the scattered light is collected and filtered, and photons related to the Raman signature of ice are detected.

Icing can be initially detected for one or more monolayers of ice. Continued observation of the signals can reveal the rate at which the ice grows.

The present disclosure further provides an aircraft icing detection system for an aircraft comprising:

(a) a Raman sensor located in the fuselage having one or a plurality of input ports and communicating with a computer to calculate vibrational changes;

(b) one or a plurality of fiber optic lines, each having a first and a second end, wherein the first end optically communicates with an input port of a Raman sensor, and the second end is focused in a direction forward to the aircraft to detect ice-laden air and air with certain temperature, humidity, and water droplet conditions.

The present disclosure provides a ground-based aircraft icing detection system comprising:

(a) a ground based laser capable of pointing onto specific sites of a passing aircraft;

(b) a ground based long-distance imaging system capable of collecting light scattered from the specific sites and transmitting said light to a light detector;

(c) a light detector device that uses dispersive elements or frequency filters to isolate photons characteristic of ice and focus those photons onto a sensor such as a photomultiplier tube, charge coupled detector or other light sensitive device.

Preferably, the light detector device is selected from the group consisting of a Raman spectrophotometer, a filter and photomultiplier tube assembly or plurality thereof, as avalanche photomultiplier tubes, photo transistors, PIN diodes, or other device that converts optical radiation to electronic, magnetic, physical or other signals, and combinations thereof.

The present disclosure further provides a process for determining ice thickness comprising:

(a) providing a lens assembly capable of translating a focal point of a Raman spectrometer;

(b) scanning said focal point through a layer of ice formed on a window, fiber tip or other transmissive element integrated into an aircraft surface; and (c) calculating the Raman signal of ice as a function of translation point in order to identify the beginning and ending positions of the ice; and (d) calculating the thickness of the ice using the beginning and ending positions of the ice.

Preferably, the focal point is moved by physically adjusting the position of the lens relative to the layer of ice. Preferably, the focal point is moved by electronically adjusting the focal length of the lens relative to the layer of ice. Preferably, the depth of field is increased across a range by increasing an F-stop or decreasing a magnification within a lens assembly. Preferably, the process further comprises calculating ice thickness by determining height of ice signal in a Raman spectrometer in view of the depth of field of the signal. Preferably, the process further comprises irradiating the aircraft surface where ice was detected with a laser or other light source to melt the ice.

In addition, the present disclosure provides a process for determining ice thickness, comprising:

(a) providing a Raman spectrometer optical detection device having a fixed focal point;

(b) providing a plurality of sensors wherein a first group of sensors are placed at one position relative to aircraft surfaces prone to icing to detect the presence of ice and a second group of sensors are placed at different positions generally orthogonal to aircraft surfaces prone to icing to detect thickness of ice formed; and (c) correlating the sensor data to determine presence and thickness of ice at the location of each sensor.

Preferably, the process further comprises irradiating the aircraft surface where ice was detected with a laser or other light source to melt the ice. More preferably, the process further comprises directing a laser or other light source to an aircraft surface to melt any ice formed on its outer surface.

DESCRIPTION OF THE FIGURES

FIG. 7 shows how one calculates the transition between ice and water by analyzing the area under the stretch and bend areas of the spectra. In this Figure, spectra are collected while a sample of ice is allowed to melt. Accordingly, when the ice melts at about 4.5 minutes, a significant increase in the area of the peak corresponding to the water bending mode is observed, and a slight increase in the area of the peak corresponding to the water stretching mode is observed. Note that a decrease in the area of a peak at 2441 cm$^{-1}$, corresponding to the H-O-D stretching mode, is observed.

Figure 1:
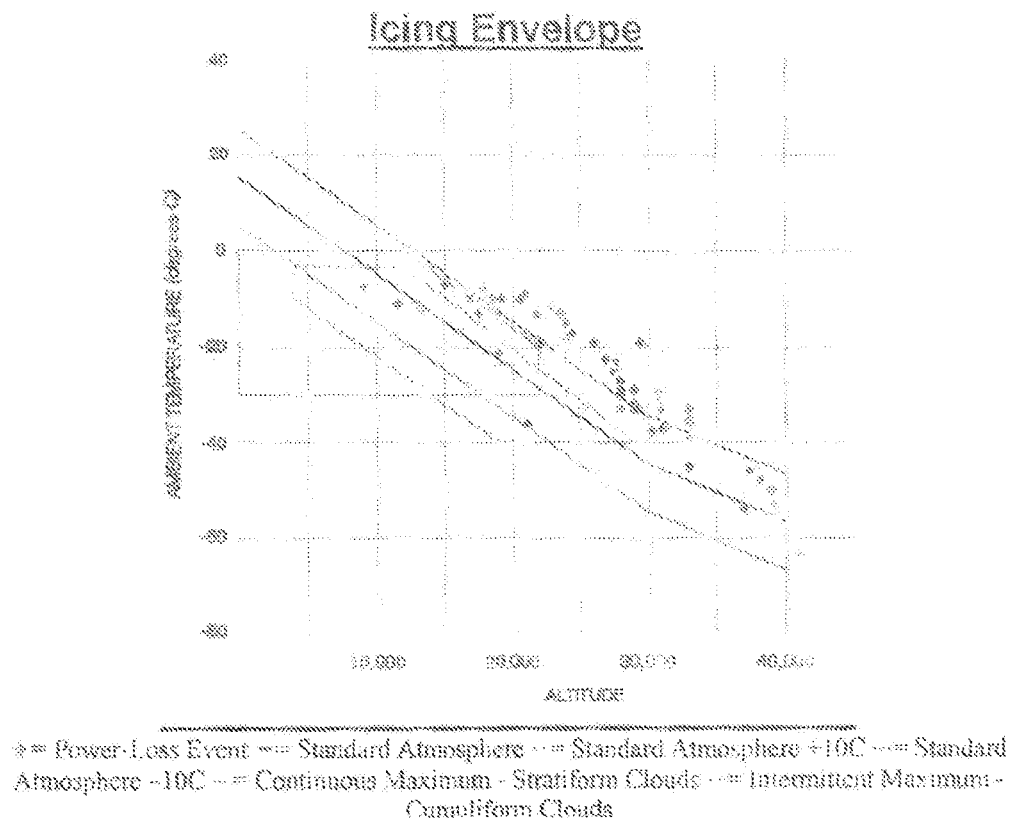
FIG. 1 shows a diagram of the altitude and temperature envelope for intermittent and continuous maximum icing conditions.
Figure 2:
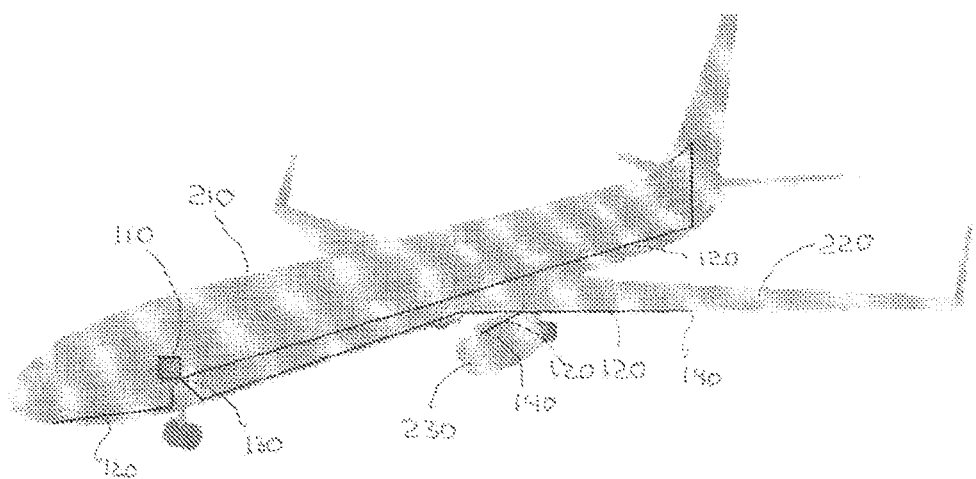
FIG. 2 is a diagram showing an example of the position of laser, Raman spectrometer and computer assembly 110, input ports 130, inside an aircraft fuselage 210, as well as examples of fiber positions comprising a light train 120 along edge of wing 220 and engine cowling 230, and a lens assembly 140.
Figure 3:
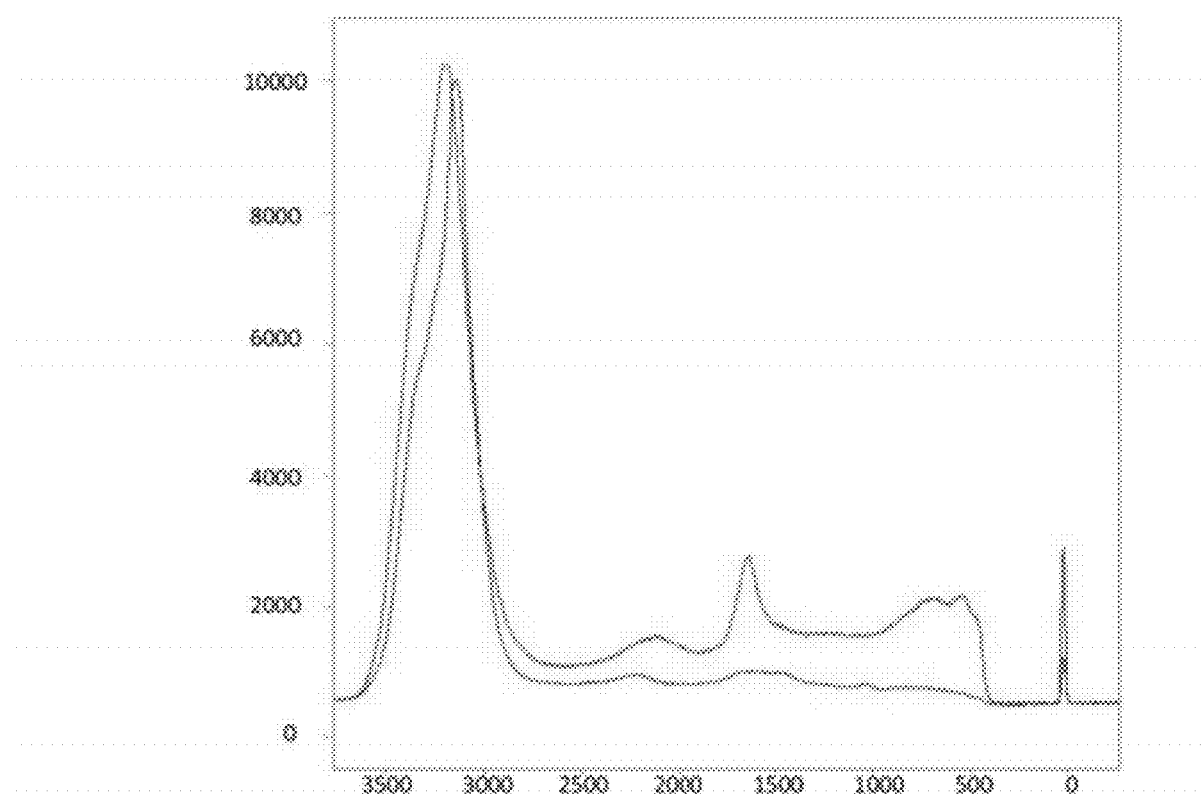
FIG. 3 is a Raman spectrum of water (red line) and ice (black line). X-axis is Raman shift, y-axis is photon counts. The water "bending" mode, represented by the band at 1625 cm$^{-1}$, is diminished in the ice spectrum. In addition, the water "stretching" mode, represented by the band at 3200 cm$^{-1}$, is shifted to lower frequency when ice is formed and changed in structure.
Figure 4:
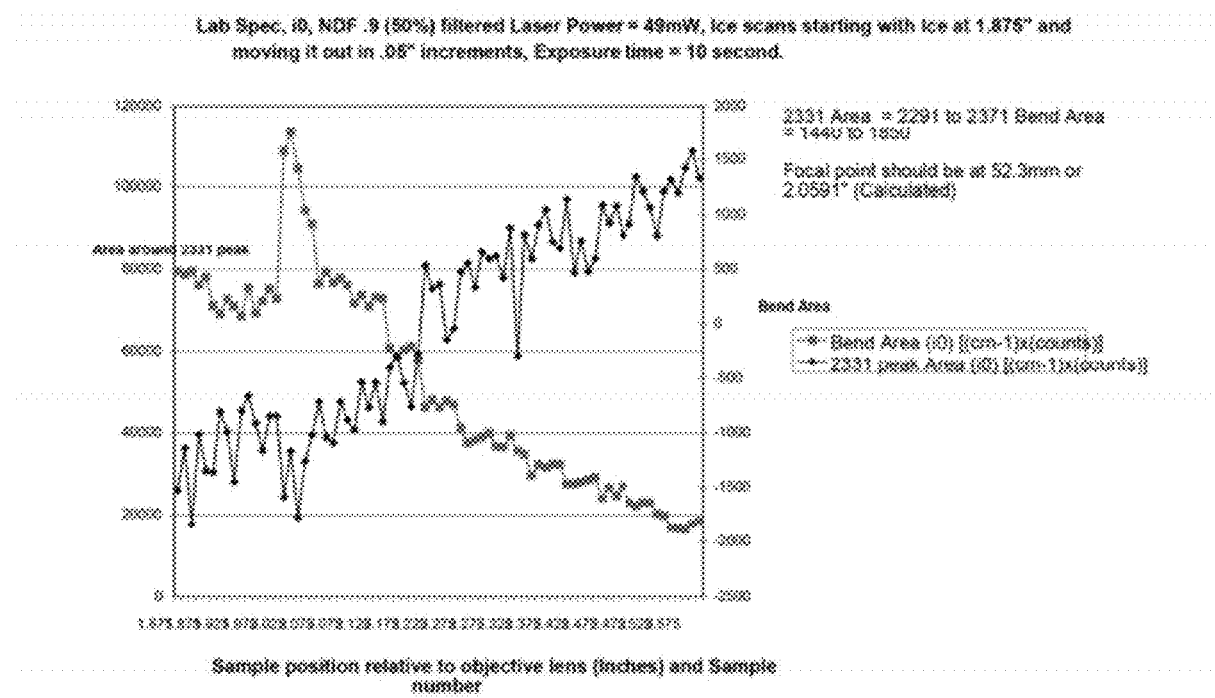
FIG. 4 shows a graph of water bend and nitrogen gas stretch peak areas versus distance between spectrometer and ice surface, as that distance is increased. Initially, the focal point of the spectrometer is located inside the ice layer. Finally, the focal point of the spectrometer is located between the spectrometer and the ice layer. As focal point is moved out of the ice layer, a spike in the water bend peak area is observed. This is likely due to liquid water present on the surface of the ice.
Figure 5:
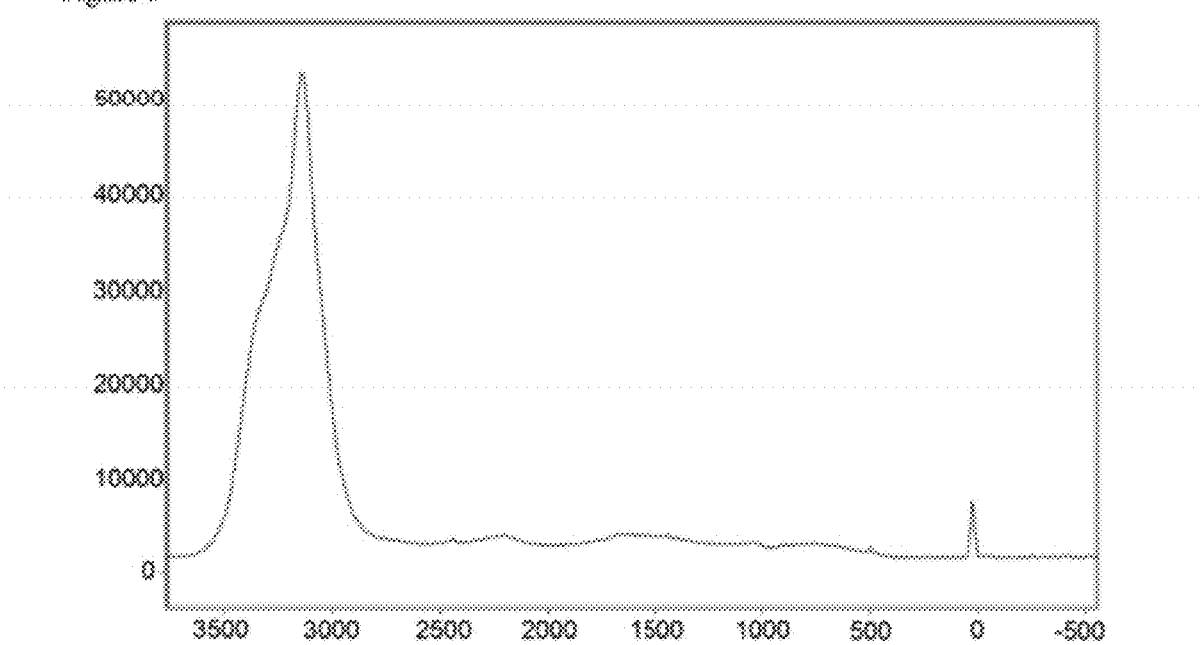
FIG. 5 is a scan showing ice with the focal point between 0.05 inches and 0.1 inches into ice. This shows the reduced peak width of the water stretching mode area and the absence of a peak at the water bending mode frequency. It is an example of an "ice" signature that one sees when ice is detected by the spectrometer.
Figure 6:
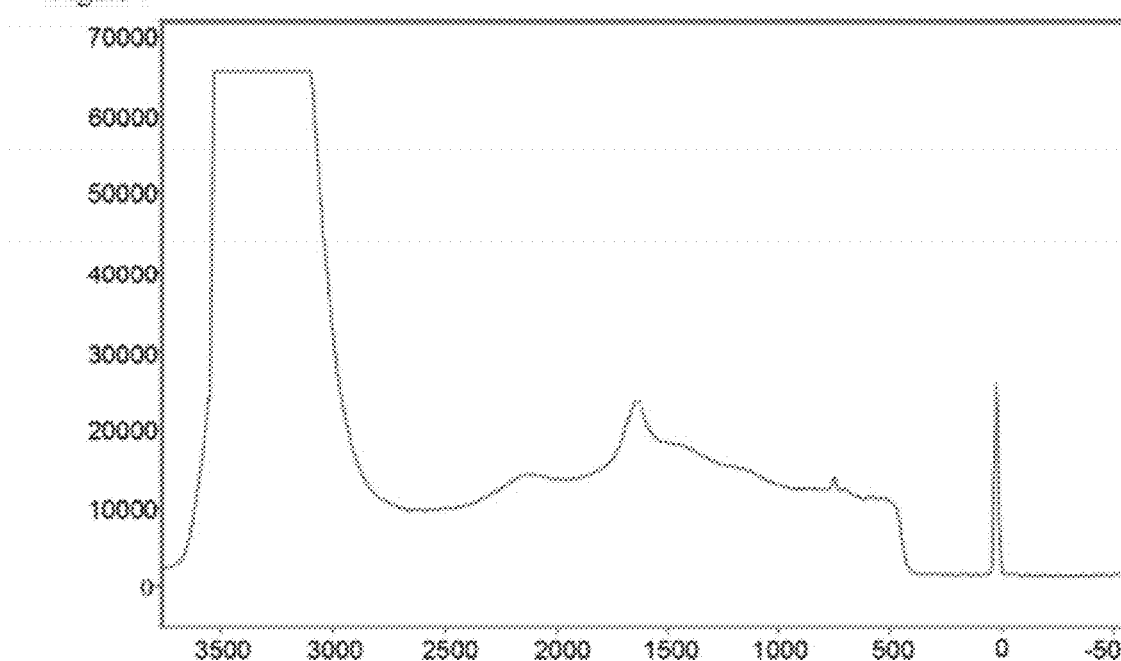
FIG. 6 shows a scan of spectra from distilled water through a sapphire window. This is the signature one sees when one scans pure water. There are differences in the stretch and bend areas when compared to the scan of FIG. 5. Note that the detector response at the frequencies corresponding to the water stretching mode is saturated in FIG. 6.
Figure 7:
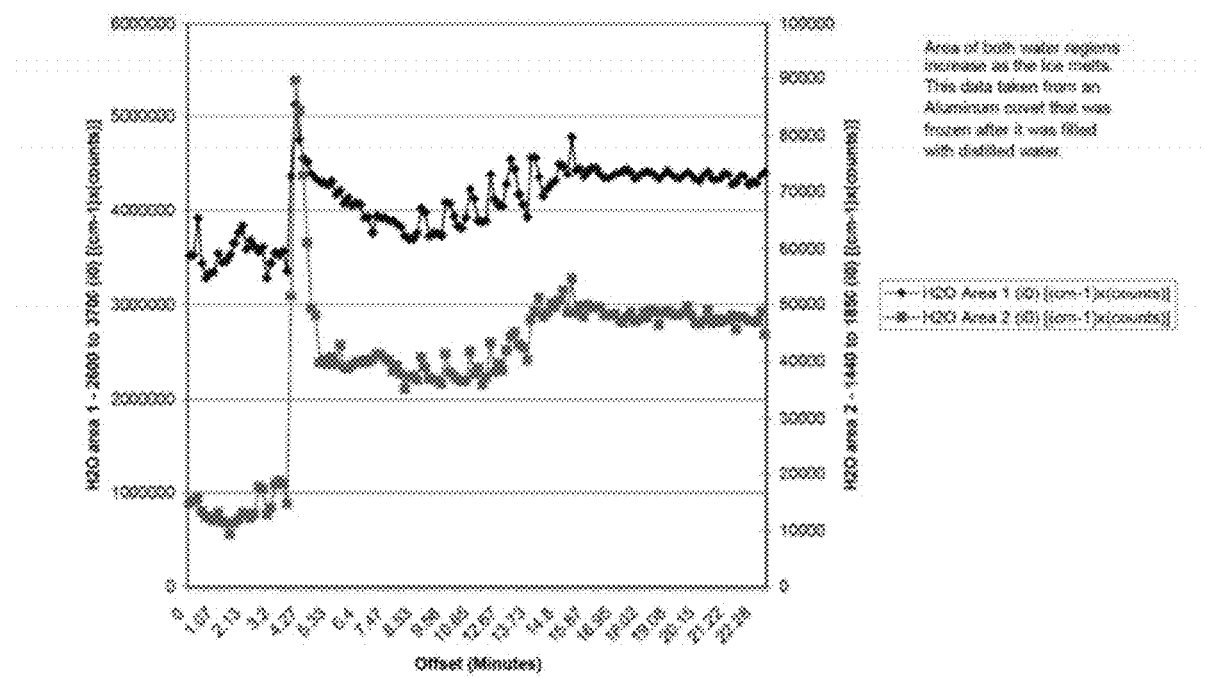
FIG. 7 provides data showing the transition between water and ice. More specifically.

(a) a ground based laser 310 capable of pointing onto specific sites of a passing aircraft;

(b) a ground based long-distance imaging system 320 capable of collecting light scattered from the specific sites and transmitting said light to a light detector; and (c) the light detector device uses dispersive elements or frequency filters 340 to isolate photons characteristic of ice and focus those photons onto a sensor 350.

DETAILED DESCRIPTION

Raman spectroscopy is a vibrational spectroscopy in which incident radiation is scattered from a molecule while it excites the bonds of the molecule. The difference in energy between the incident and scattered radiation reveals the quantum of energy that interacted with the bonds or groups of bonds. That quantum of energy is typically unique to a bond or group of bonds. By observing the quantum of energy that interacted with a molecule, the identity of the molecule can typically be established. By observing the number of photons that are changed in energy after encountering a sample, the concentration of the molecules can be further established.

Water has a relatively low scattering cross-section. Therefore, water does not exhibit an extremely large Raman effect. As a result, Raman spectroscopy is useful when detecting analytes present in high humidity or liquid aqueous environments, such as detecting the formation of ice in high humidity atmospheric environments.

Another feature of Raman spectroscopy is that the excitation and collection photons are managed, filtered and transmitted using standard optical apparatus. As a result, a delicate laser and spectrometer apparatus can be located remotely from a sample, particularly when the sample occurs in harsh environments.

This disclosure provides a method and apparatus for early detection of icing. It is suitable for use in aircraft, boats, oil rigs, wind turbines, and the like. Preferably, it can be used in aircraft to detect early signs of icing on wing, sensor or engine surfaces, or on other key surface locations of aircraft. The present disclosure provides an aircraft icing detection system for an aircraft having fuselage, one or a plurality of engines and wings, comprising:

(a) a Raman sensor located in the fuselage having a plurality of input ports and communicating with a computer to calculate vibrational changes;

(b) a plurality of fiber optic lines, each having a first and a second end, wherein the first end optically communicates with an input port of a Raman sensor, and the second end is focused on a structure located on a wing surface or an engine surface.

Preferably, the Raman spectrometer is located in the cargo area of the aircraft. Preferably, there are from about two to about one hundred fiber optic lines, each leading to various positions on the aircraft that tend to ice, including, but not limited to, forward wing edges and the engine intake manifolds. More preferably, there are from about 15 to about 30 fiber optic lines.

The present disclosure provides a process for detecting one or more molecular monolayers of greater amounts of ice formed on a surface, comprising:

(a) providing an aircraft with a Raman sensor located in the fuselage having a plurality of input ports and communicating with a computer to calculate vibrational changes, and a plurality of fiber optic lines, each having a first and a second end, wherein the first end optically communicates with an input port of a Raman sensor, and the second end is focused on a structure located on a wing surface or an engine surface; and (b) reading each fiber optic line to detect ice formed on the surface.

Preferably, the Raman spectrometer focuses an exciting laser beam onto the surface of the structure of interest, the scattered light is collected and filtered, and photons related to the Raman signature of ice are detected. In particular, the O-H bending mode of liquid water shifts in frequency to lower energy when the water is frozen. This shift can be used as an indication of ice formation.

Icing can be initially detected one or more monolayers of ice. Continued observation of the signals can reveal the rate at which the ice grows.

Measuring Ice Thickness

Aircraft ice thickness can range from 10 nm to 5 cm or more thick. One way to measure ice thickness is to establish an optical excitation/collection geometry with a known depth of field, and then calibrate the number of photons at the Raman shift frequency or frequencies characteristic of ice to the thickness of the ice that caused them.

Therefore, there is disclosed a process for determining ice thickness on an aircraft comprising:

(a) providing an optical assembly capable of delivering a laser beam radiation to a sample and collecting scattered radiation from said sample, wherein such assembly has been calibrated for the relationship between the thickness of one or more ice layers and the Raman signal that they cause;

(b) observing the scattered radiation to obtain a Raman signal of ice; and (c) using the calibration to calculate the thickness of the ice as a function of the Raman signal observed.

Preferably, the calibration is repeated for a number of different thicknesses of ice and for a number of different types of ice, such as glaze, glime and rime. Preferably, the Raman signal of the ice layer is also used to select the appropriate calibration to use in the calculation of thickness; e.g. if the baseline levels of the Raman spectra are high, then the rime ice calibration is used in the calibration. Preferably, results from measurement or measurements of the surrounding air temperature or other characteristics such as water droplet size, humidity, etc. are used to select the appropriate calibration to use in the calculation of thickness. Preferably, the assembly is used to monitor the accretion of ice over time and thereby calculate a rate of accretion that can be provided to a computer, operator or pilot. Preferably, by measuring the ratio of the photons at the O-H stretching mode frequency to those at the O-H bending mode frequency, it is possible to judge the amount of ice that is present. For example, when such a ratio increases in magnitude, the more ice is present. When the ratio decreases in magnitude, less ice is present.

In the case where the ice thickness exceeds the depth of field of the optical assembly, so that additional accretion of ice does not result in increase Raman signal, an alternate optical assembly is employed in which multiple excitation/collection elements are designed, fabricated, and/or positioned so that the dynamic ranges of their responses to ice thickness overlap in such a manner to increase the dynamic range of the overall assembly. Preferably, a series of fiber optics are fabricated with a variety of focal lengths and then placed into a bundle that is used in aggregate to collect radiation from the sample. In this manner, fiber optics with shorter focal lengths are sensitive to thinner ice accretions but not thicker ice accretions, while fiber optics with longer focal lengths are sensitive to thicker ice accretions but not thinner ice accretions. By measuring the signals from all fiber optics concurrently, both thinner and thicker accretions of ice can be measured and the dynamic range of the overall assembly can be increased.

Aircraft ice thickness can range from 10 nm to 5 cm or more thick. One way to measure ice thickness is to measure the focal point of laser to move it across the ice and get a graph of Raman photons collected versus translational distance. Therefore, a process for determining ice thickness on an aircraft comprising:

(a) providing a lens assembly capable of translating a focal point of a Raman spectrometer;

(b) scanning said the lens across focal points through a layer of ice formed on a window, fiber tip or other transmissive element integrated into an aircraft surface to obtain a Raman signal of ice;

(c) calculating the Raman signal of ice as a function of translation point in order to identify the beginning and ending positions of the ice; and (d) calculating the thickness of the ice using the beginning and ending positions of the ice.

Preferably, the focal point is moved by physically adjusting the position of the lens assembly relative to the layer of ice. Preferably, the focal point is moved by electronically adjusting the focal length of the lens relative to the layer of ice using an electro-optic lens. Preferably, the process further comprises increasing depth of field across a range by increasing an F-stop or decreasing a magnification within a lens assembly. Preferably, the process further comprises calculating ice thickness by determining height of ice signal in a Raman spectrometer in view of the depth of field of the signal. Preferably, the process further comprises irradiating aircraft surface where ice was detected with a laser or other light source to melt the ice.

Alternatively, the present disclosure provides a process for determining ice thickness, comprising:

(a) providing a Raman spectrometer optical detection device having a fixed focal point;

(b) providing a plurality of sensors wherein a first group of sensors are placed at one position relative to aircraft surfaces prone to icing to detect the presence of ice and a second group of sensors are placed at different positions generally orthogonal to aircraft surfaces prone to icing to detect thickness of ice formed; and (c) correlating the sensor data to determine presence and thickness of ice at the location of each sensor.

Preferably, the process further comprises irradiating the aircraft surface where ice was detected with a laser or other light source to melt the ice. More preferably, the process further comprises directing a laser or other light source to an aircraft surface to melt any ice formed on its outer surface. Preferably, the plurality of sensors are selected from the group consisting of a Raman spectrophotometer, a photomultiplier tube, charge coupled camera device, as avalanche photomultiplier tubes, photo transistors, PIN diodes, or other device that converts optical radiation to electronic, magnetic, physical or other signals and combinations thereof.

Type of Ice

The present disclosure provides a process for determining the type of ice present on an aircraft while in flight. More specifically, rime ice will reflect light as it scatters. However, glaze ice will not scatter light. Glaze ice often cannot be seen with the naked eye, but a Raman reading from glaze ice will detect its presence in situ. The Raman spectra collected can be further evaluated in order to determine whether the ice that accretes is glaze or rime ice. Glaze or rime ice can also be determined by evaluating the backscattering of the incident radiation at the fiber tip, since glaze ice is more optically transparent and does not backscatter radiation to the extent that rime ice does. After the system describes an icing event, and the aircraft returns to flight conditions under which icing does not occur, the laser continues to exit the fiber tip and heat any covering ice, thereby melting the ice and returning the tip to its original configuration. In some cases, the laser power may be increased at this time in order to accelerate such melting. In cases where the fiber tip cannot be returned to a condition that provides the original optical throughput or spectra features, that fiber can be identified for maintenance or cleaning upon landing.

The present disclosure provides a process for determining the type of ice present on aircraft surfaces when ice has been detected, comprising:

(a) measuring reflectivity or transmissivity of ice on aircraft surfaces; and (b) determining molecular structure of the ice from the frequencies and/or amplitudes of vibrational bands identified in the Raman spectra of such ice.

Distributed Sensor System

The present disclosure further provides a distributed sensing system for measuring the presence of, thickness of and type of ice at multiple aircraft surfaces subject to icing, comprising:

(a) providing a plurality of Raman spectrophotometers at multiple surface sites on an aircraft that are subject to icing, wherein each Raman spectrophotometer comprises a light source and a detector source and an electronic output to report the Raman spectra obtained at each time interval; and (b) a central computing device, wherein each computing device communicates with each distributed Raman spectrophotometer to calculate differences in the spectra obtained at each distributed site.

Mitigating Interfering Signals

The present disclosure further provides a process for mitigating interfering signals by utilizing one or more internal standards and/or calibration methods, comprising:

(a) obtaining an internal standard signal for a fiber tip or optical window;

(b) obtaining an internal signal standard from nitrogen gas in air surrounding the aircraft;

(c) determining backscatter to indicate window-to-air interfacial quality;

(d) determining background light levels to indicate window-to-air interfacial quality;

(e) calibrating a sample of ice or other solid against the windshield to determine ice signatures; and (f) filtering surrounding sunlight or averaging or co-adding spectra to remove background sunlight.

Other spectral features are observed in order to evaluate the calibration and optical throughput of each fiber and qualify or disqualify the Raman signals resulting from such fiber. The other spectral features include, for example, the Raman signature of nitrogen gas, the broadband signature of sunlight, the Raman or absorption signal of the optical fiber or other optical components, the Raman or absorption signal of the protective window, and the baseline spectral background indicating non-Raman scattering from the fiber tip or protective window, among others.

The Raman spectra collected can be further evaluated in order to determine whether the ice that accretes is glaze or rime ice. Glaze or rime ice can also be determined by evaluating the backscattering of the incident radiation at the window, since glaze ice is more optically transparent and does not backscatter radiation to the extent that rime ice does. After the system describes an icing event, and the aircraft returns to flight conditions under which icing does not occur, the laser continues to exit the fiber tip and heat any covering ice, thereby melting the ice and returning the window to its original configuration. In some cases, the laser power may be increased at this time in order to accelerate such melting. In cases where the window cannot be returned to a condition that provides the original optical throughput or spectra features, that position can be identified for maintenance or cleaning upon landing.

By measuring the ratio of the photons at the O-H stretching mode frequency to those at the O-H bending mode frequency, it is possible to judge the amount of ice that is present. For example, when such a ratio increases in magnitude, the more ice is present. When the ratio decreases in magnitude, less ice is present.

Ground-Based Aircraft Icing Detector Device

The present disclosure provides a ground-based aircraft icing detection system comprising:

(a) a ground based laser capable of pointing onto specific sites of a passing aircraft;

(b) a ground based long-distance imaging system capable of collecting light scattered from the specific sites and transmitting said light to a light detector; and (c) a light detector device that uses dispersive elements or frequency filters to isolate photons characteristic of ice and focus those photons onto a sensor.

Preferably, the light detector device is selected from the group consisting of a Raman spectrophotometer, a filter and photomultiplier tube assembly or plurality thereof, a charge coupled detector, and combinations thereof.

Aircraft Sensor Configurations

In one embodiment, a Raman spectrometer/laser assembly is located in the cargo area of an airplane. A 532 nm frequency doubled NdYAG laser beam is optically coupled into from five to thirty 200 μm optical fibers that each lead from the spectrometer/laser assembly through the internal spaces of the aircraft to various internal positions. The internal positions are chosen to be immediately inside the external surfaces that typically accumulate ice when an aircraft encounters icing conditions. Preferably, at least four optical fibers lead to internal positions distributed around each engine cowling; three fibers lead to internal positions distributed along each leading wing edge; two fibers lead to internal positions distributed along the leading edge of the vertical stabilizer section of the tail; two fibers lead to internal positions distributed along the leading edge of each of the horizontal stabilizer sections of the tail; two fibers lead to internal positions in the aircraft nose cone; and four fibers lead to internal positions distributed within key aircraft sensors such as air speed sensors.

At each internal position, the fibers are terminated with optically transparent tips, either by coupling the fiber to a lens or other optical component or by polishing the fiber itself to create an optically transmissive termination point. The tips are then physically integrated into the external aircraft surfaces so that the optically transmissive terminal surface is substantially flush with the surrounding aircraft surface. In some cases, the tips may be inset or outset from the aircraft surface in order to accelerate or decelerate icing accumulation on the tips as compared to that on the surrounding aircraft surfaces.

The optical properties of the tips are created in such a manner that the excitation light is focused with a focal length of preferably about one millimeter from the tip and depth of field of preferably about two centimeters. Preferably, each fiber may actually be an assembly of two or more fibers in which one approximately 100 μm fiber carries the laser excitation radiation and one or more approximately 200 μm fibers carry the radiation scattered from the sample. For example, the couplings to the spectrograph and to the aircraft surface may be accomplished using optical probes containing windows, lenses or other optical components. In some cases, the fibers or fiber assemblies may be jacketed in protective sleeves in order to protect them from physical damage or to improve their optical properties. In some cases the tips may be chemically or physically treated, or covered with high pressure windows made from, e.g., sapphire, in order to protect the fiber tips from harsh conditions or to accelerate or decelerate icing accumulation on the tips as compared to that on the surrounding aircraft surfaces. The fibers intersect the outside surfaces and are preferably positioned in such a way so that the tips of the fibers are substantially flush with the outside surfaces. The excitation light exits the fiber ends. When ice begins to build on the surfaces, and on the fiber tips, the ice Raman scatters the excitation light and thereby changes the frequency of some of the photons in that light, the fiber tip collects the scattered light, and the photons signature of the Raman response of ice are then transmitted back down the fiber to the spectrometer. At the spectrograph, each fiber is positioned vertically so that it can be handled separately and eventually imaged onto a discrete horizontal area of the detector.

The scattered light is filtered to remove light at a preferred excitation laser frequency of 532 nm. The scattered light is then passed through an optical element, such as a prism, or reflected from an optical element, such as a grating, that distributes the photons in the light substantially horizontally according to frequency. The distributed photons for all 26 or so fibers are then directed at a detector, such as a charge coupled device, so that each fiber provides a spectrum of light along 26 or so rows of the charge coupled device. In some cases, intervening rows are left dark in order to reduce crosstalk.

Each row in the detector device is then read out electronically so that about 26 spectra are generated, each corresponding to a different position on the aircraft surfaces. The spectra are then evaluated for photons at frequencies characteristic of ice in order to indicate the presence of ice at a particular position on the aircraft surfaces. In some cases, longer exposure times may be taken, or multiple spectra may be co-added, in order to reduce effectively random noise in the detector. In this way, smaller numbers of photons, characteristic of ice, can be observed. The spectra are evaluated over time for the number of photons characteristic of ice in order to calculate how much ice has accumulated and the rate at which ice is accumulating.

Laser-induced melting of accumulated ice is accounted for when modeling the increase in ice photons collected over time. Preferably, the number of photons collected at a frequency characteristic of ice is ratio'ed to those collected at a frequency characteristic of some other component or internal standard in the system in order to remove variation and drift in spectral response of the system.

The frequency and intensity of the Raman photons are measured and recorded for each fiber, each representing discrete outside surface locations of the aircraft. The results are transmitted to the pilots, the flight computer, and/or other entities. Other spectral features are observed in order to evaluate the calibration and optical throughput of each fiber and qualify or disqualify the Raman signals resulting from such fiber. These features include, for example, the Raman signature of nitrogen gas, the broadband signature of sunlight, the Raman or absorption signal of the optical fiber or other optical components, the Raman or absorption signal of the protective window, and the baseline spectral background indicating non-Raman scattering from the fiber tip or protective window, among other.

In other embodiments, a spectrometer is not used. Instead, the laser beam is directed via one or more optical fibers to the outside surface(s) of interest. Scattered Raman light is collected. A notch filter, built to reject all light except photons at the frequency represented by the peak of the ice stretching O-H band, is used to filter the light. The transmitted photons are directed onto a light sensor such as a photomultiplier tube. When the sensor detects a larger number of photons, the presence of ice on the surface is thus confirmed. Progressive, serial excitation of multiple fibers can be correlated to temporal response of the sensor in order to quickly evaluate multiple aircraft surfaces. Such serial excitation can occur in a high frequency mode of 10 Hertz or faster or a low frequency mode of 10 Hertz or slower.

In another embodiment, a Raman spectrometer/laser assembly is located in the cargo area of an airplane. A 532 nm frequency doubled NdYAG laser beam is optically coupled into twenty-six 200 μm optical fibers that lead from the spectrometer/laser assembly through the internal spaces of the aircraft to various internal positions. The internal positions are chosen to be immediately inside the external surfaces that typically accumulate ice when the aircraft encounters icing conditions. In this embodiment, four fibers lead to internal positions distributed around each engine cowling; three fibers lead to internal positions distributed along each leading wing edge; two fibers lead to internal positions distributed along the leading edge of the vertical stabilizer section of the tail; two fibers lead to internal positions distributed along the leading edge of each of the horizontal stabilizer sections of the tail; two fibers lead to internal positions in the aircraft nose cone; and four fibers lead to internal positions distributed within key aircraft sensors such as air speed sensors. At each internal position, the fibers are terminated with optically transparent tips, either by coupling the fiber to a lens or other optical component or by simply polishing the fiber itself to create an optically transmissive termination point.

A window is then physically integrated into the external aircraft surfaces so that the optically transmissive terminal surface is flush with the surrounding aircraft surface to outset with the surrounding surface. In some cases, the windows may be inset or outset from the aircraft surface in order to accelerate or decelerate icing accumulation on the windows as compared to that on the surrounding aircraft surfaces. The optical properties of the tips are created in such a manner that the excitation light is focused with a focal length of approximately one centimeter from the tip and depth of field of about five millimeters. The tip is then integrated with the window using a mechanical translation stage that allows the focal point of the tip to be moved from inside the window itself to five millimeters outside the window. In some cases, an electro-optic component may be use to electronically change the curvature of the final lens, and thus the focal length and depth of field, for the tip. In some cases, each fiber may actually be an assembly of two fibers in which one 100 μm fiber carries the laser excitation radiation and one 200 μm fiber carries the radiation scattered from the sample. In some cases, the couplings to the spectrograph and to the aircraft surface may be accomplished using optical probes containing windows, lenses or other optical components. In some cases, the fibers or fiber assemblies may be jacketed in protective sleeves in order to protect them from physical damage or to improve their optical properties. In some cases the windows may be chemically or physically treated in order to protect the windows from harsh conditions or to accelerate or decelerate icing accumulation on the windows as compared to that on the surrounding aircraft surfaces.

The windows intersect the outside surfaces and are preferably positioned in such a way so that the tips of the fibers are flush with the outside surfaces. During operation, the excitation light exits the fiber ends and the windows. When ice begins to build on the surfaces, and on the windows, the ice Raman scatters the excitation light and thereby changes the frequency of some of the photons in that light, the fiber tip collects the scattered light, and the photons signature of the Raman response of ice are then transmitted back down the fiber to the spectrometer. At the spectrograph, each fiber is positioned vertically so that it can be handled separately and eventually imaged onto a discrete horizontal area of the detector. The scattered light is filtered to remove light at the excitation laser frequency of 532 nm, and the scattered light is then passed through an optical element such as a prism or reflected from an optical element such as a grating that distributes the photons in the light horizontally according to frequency. The distributed photons for the 26 fibers are then directed at a charge coupled device so that each fiber provides a spectrum of light along 26 rows of the charge coupled device. In some cases, intervening rows are left dark in order to reduce crosstalk. Each row is then read out electronically so that 26 spectra are generated, each corresponding to a different position on the aircraft surfaces.

The spectra are then evaluated for photons at frequencies characteristic of ice in order to indicate the presence of ice at a particular position on the aircraft surfaces. In some cases, longer exposure times may be taken, or multiple spectra may be co-added, in order to reduce effectively random noise in the detector, so that smaller numbers of photons characteristic of ice can be observed. The spectra are evaluated as the focal point of the incident radiation is translated from inside the window to five millimeters outside the window for the number of photons characteristic of ice in order to calculate the thickness of accumulated ice and the rate at which ice is accumulating. Laser-induced melting of accumulated ice is accounted for when modeling the increase in ice photons collected over time. In some cases, the number of photons collected at a frequency characteristic of ice is ratio'ed to those collected at a frequency characteristic of some other component or internal standard in the system in order to remove variation and drift in spectral response of the system. The frequency and intensity of the Raman photons are measured and recorded for each fiber, each representing discrete outside surfaces of the aircraft. The results are transmitted to the pilots, the flight computer, and/or other entities.

In another embodiment, a notch filter/photomultiplier tube assembly is located in the cargo area of an airplane. A 532 nm frequency doubled NdYAG laser beam is optically coupled into about twenty-six 200 μm optical fibers that lead from the assembly through the internal spaces of the aircraft to various internal positions. In some cases, optical coupling of the laser to the fibers is accomplished serially so that at any one time only one fiber is coupled to the laser. The internal positions are chosen to be immediately inside the external surfaces that typically accumulate ice when the aircraft encounters icing conditions. Accordingly, four fibers lead to internal positions distributed around each engine cowling; three fibers lead to internal positions distributed along each leading wing edge; two fibers lead to internal positions distributed along the leading edge of the vertical stabilizer section of the tail; two fibers lead to internal positions distributed along the leading edge of each of the horizontal stabilizer sections of the tail; two fibers lead to internal positions in the aircraft nose cone; and four fibers lead to internal positions distributed within key aircraft sensors such as air speed sensors.

At each internal position, the fibers are terminated with optically transparent tips, either by coupling the fiber to a lens or other optical component or by simply polishing the fiber itself to create an optically transmissive termination point. The tips are then physically integrated into the external aircraft surfaces so that the optically transmissive terminal surface is flush with the surrounding aircraft surface. In some cases, the tips may be inset or outset from the aircraft surface in order to accelerate or decelerate icing accumulation on the tips as compared to that on the surrounding aircraft surfaces.

The optical properties of the tips are created in such a manner that the excitation light is focused with a focal length of about one millimeter from the tip and depth of field of about two centimeters. In some cases, each fiber may actually be an assembly of two fibers in which one 100 μm fiber carries the laser excitation radiation and one 200 μm fiber carries the radiation scattered from the sample. In some cases, the couplings to the filter/photomultiplier tube assembly and to the aircraft surface may be accomplished using optical probes containing windows, lenses or other optical components. In some cases, the fibers or fiber assemblies may be jacketed in protective sleeves in order to protect them from physical damage or to improve their optical properties. In some cases the tips may be chemically or physically treated, or covered with high pressure windows made from, for example, sapphire, in order to protect the tips from harsh conditions or to accelerate or decelerate icing accumulation on the tips as compared to that on the surrounding aircraft surfaces. The fibers intersect the outside surfaces of the aircraft and are preferably positioned in such a way so that the tips of the fibers are flush with the outside surfaces. The excitation light exits the fiber ends.

When ice begins to build on the surfaces, and on the fiber tips, the ice Raman scatters the excitation light and thereby changes the frequency of some of the photons in that light, the fiber tip collects the scattered light. The photons that form a signature of the Raman response of ice are then transmitted back down the fiber to the sensing assembly. At the sensing assembly, each fiber is positioned so that it is incident on a notch filter, which is transmissive only to radiation from about 500 to about 3500 $cm^{-1}$ less than the excitation light frequency, and the photomultiplier tube at a known time. The signal from each fiber is then read by the photomultiplier tube at a particular time that is known to correspond to a particular location on the aircraft surface. The signals at each time are repeatedly evaluated in order to calculate how much ice has accumulated at each position and the rate at which ice is accumulating at each position.

Laser-induced melting of accumulated ice is accounted for when modeling the increase in ice photons collected over time. The results are transmitted to the pilots, the flight computer, and/or other entities.

Other optical features are observed in order to evaluate the calibration and optical throughput of each fiber and qualify or disqualify the Raman signals resulting from such fiber. These features include the broadband signature of sunlight, the absorption signal of the optical fiber or other optical components, the absorption signal of the protective window, and the baseline background indicating non-Raman scattering from the fiber tip or protective window, among other. After the system describes an icing event, and the aircraft returns to flight conditions under which icing does not occur, the laser continues to exit the fiber tip and heat any covering ice, thereby melting the ice and returning the tip to its original configuration. In some cases, the laser power may be increased at this time in order to accelerate such melting. In cases where the fiber tip cannot be returned to a condition that provides the original optical throughput, that fiber can be identified for maintenance or cleaning upon landing.

In some cases, such a filter and sensor system can be deployed at each location of interest in the aircraft. In such cases, each system can communicate electronically with a central computer or other operator interface, obviating the need for installing long optical fibers throughout the aircraft. In this manner, light losses and optical variability due to long optical fibers can be reduced or eliminated.

In another embodiment, a notch filter/photomultiplier tube assembly is located at 26 internal positions in an airplane. At each position, a 532 nm frequency doubled NdYAG laser beam is optically coupled into a 200 μm optical fiber that leads from the assembly through the external aircraft surface at the position. Each internal position is chosen to be immediately inside an external surface that typically accumulates ice when the aircraft encounters icing conditions. Accordingly, in this embodiment, four internal positions are distributed around each engine cowling; three internal positions are distributed along each leading wing edge; two internal positions are distributed along the leading edge of the vertical stabilizer section of the tail; two internal positions are distributed along the leading edge of each of the horizontal stabilizer sections of the tail; two internal positions are distributed in the aircraft nose cone; and four internal positions are distributed within key aircraft sensors such as air speed sensors.

At each internal position, the fiber is terminated with an optically transparent tip, either by coupling the fiber to a lens or other optical component or by simply polishing the fiber itself to create an optically transmissive termination point. The tip is then physically integrated into the external aircraft surface so that the optically transmissive terminal surface is flush with the surrounding aircraft surface. In some cases, the tip may be inset or outset from the aircraft surface in order to accelerate or decelerate icing accumulation on the tip as compared to that on the surrounding aircraft surface. The optical properties of the tip are created in such a manner that the excitation light is focused with a focal length of one millimeter from the tip and depth of field of two centimeters. In some cases, the fiber may actually be an assembly of two fibers in which one 100 μm fiber carries the laser excitation radiation and one 200 μm fiber carries the radiation scattered from the sample. In some cases, the coupling to the filter/photomultiplier tube assembly and to the aircraft surface may be accomplished using an optical probe containing windows, lenses or other optical components. In some cases, the fiber or fiber assembly may be jacketed in protective sleeves in order to protect it from physical damage or to improve its optical properties. In some cases the tip may be chemically or physically treated, or covered with a high pressure window made from, for example, sapphire, in order to protect the tip from harsh conditions or to accelerate or decelerate icing accumulation on the tip as compared to that on the surrounding aircraft surface. The fiber intersects the outside surface and is preferably positioned in such a way so that the tip of the fiber is flush with the outside surface. The excitation light exits the fiber end.

When ice begins to build on the surfaces, and on the fiber tip, the ice Raman scatters the excitation light and thereby changes the frequency of some of the photons in that light, the fiber tip collects the scattered light, and the photons signature of the Raman response of ice are then transmitted back down the fiber to the sensing assembly. At the sensing assembly, the fiber is positioned so that it is incident on a notch filter, which is transmissive only to radiation from about 500 to about 3500 cm$^{-1}$ less than the excitation light frequency, and the photomultiplier tube at a known time. The filtered signal from the fiber is then read by the photomultiplier tube. The signal is repeatedly evaluated in order to calculate how much ice has accumulated and the rate at which ice is accumulating.

Laser-induced melting of accumulated ice is accounted for when modeling the increase in ice photons collected over time. The results are transmitted to the pilots, the flight computer, and/or other entities. Other optical features are observed in order to evaluate the calibration and optical throughput of the fiber and qualify or disqualify the Raman signals resulting from the fiber and sensing assembly. These features include the broadband signature of sunlight, the absorption signal of the optical fiber or other optical components, the absorption signal of the protective window, and the baseline background indicating non-Raman scattering from the fiber tip or protective window, among other. After the system describes an icing event, and the aircraft returns to flight conditions under which icing does not occur, the laser continues to exit the fiber tip and heat any covering ice, thereby melting the ice and returning the tip to its original configuration. In some cases, the laser power may be increased at this time in order to accelerate such melting. In cases where the fiber tip cannot be returned to a condition that provides the original optical throughput, that fiber can be identified for maintenance or cleaning upon landing.

In some cases, optical fibers may not be used to transmit the incident and scattered light. Instead, the spectrometer or filter and sensor system are positioned so that the incident and scattered light follow one or more open light paths that are established by mirrors, lenses and filters. In this manner, greater light throughput can be achieved for the system.

In another embodiment, a notch filter/photomultiplier tube assembly or spectrograph is located at 26 internal positions in an airplane. At each position, a 532 nm frequency doubled NdYAG laser beam is directed at a sapphire window inset into the aircraft skin so that optical transmission from inside the aircraft to outside the aircraft can occur. Each internal position is chosen to be immediately inside an external surface that typically accumulates ice when the aircraft encounters icing conditions. Accordingly, four internal positions are distributed around each engine cowling; three internal positions are distributed along each leading wing edge; two internal positions are distributed along the leading edge of the vertical stabilizer section of the tail; two internal positions are distributed along the leading edge of each of the horizontal stabilizer sections of the tail; two internal positions are distributed in the aircraft nose cone; and four internal positions are distributed within key aircraft sensors such as air speed sensors. The window is physically integrated into the external aircraft surface so that the optically transmissive terminal surface is flush with the surrounding aircraft surface. In some cases, the window may be inset or outset from the aircraft surface in order to accelerate or decelerate icing accumulation on the window as compared to that on the surrounding aircraft surface. The optical properties of the light path are created using lenses, mirrors and windows so that the excitation light is focused with a focal length of one millimeter from the tip and depth of field of two centimeters. In some cases, the optical path may be jacketed in order to reduce or eliminate external radiation. In some cases the window may be chemically or physically treated in order to protect it from harsh conditions or to accelerate or decelerate icing accumulation on the window as compared to that on the surrounding aircraft surface. During operation, the excitation light exits the window.

Figure 8:
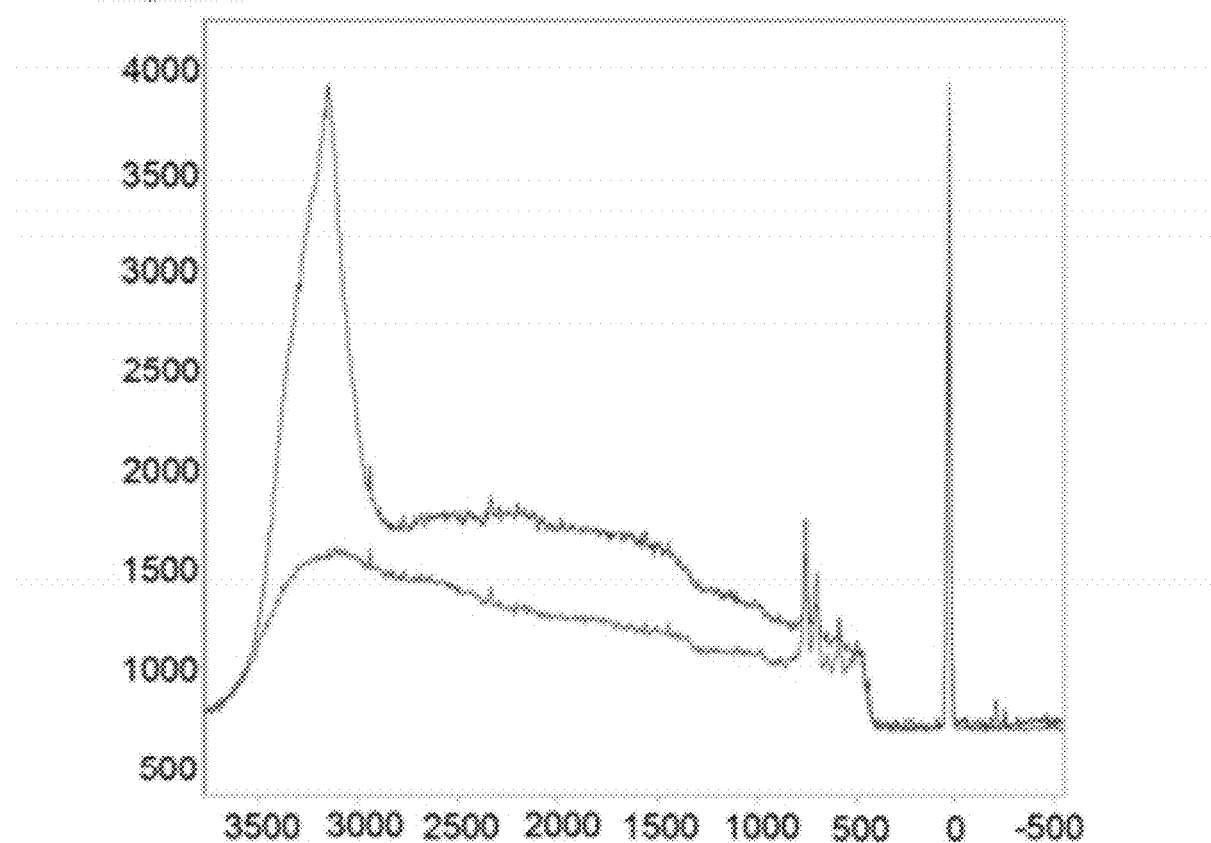
FIG. 8 shows spectra collected before and after onset of icing for an open beam path embodiment. The background characters of the spectra are generated by spectral contributions from a sapphire window on which ice was accreted. That background characters can be used as a convenient internal standard to calibrate spectrometer throughput. In addition, some light from the incident laser remained unfiltered and is shown at 0 cm$^{-1}$. Such laser light is a convenient internal standard to calibrate the frequency response of the spectrometer.
Figure 9:
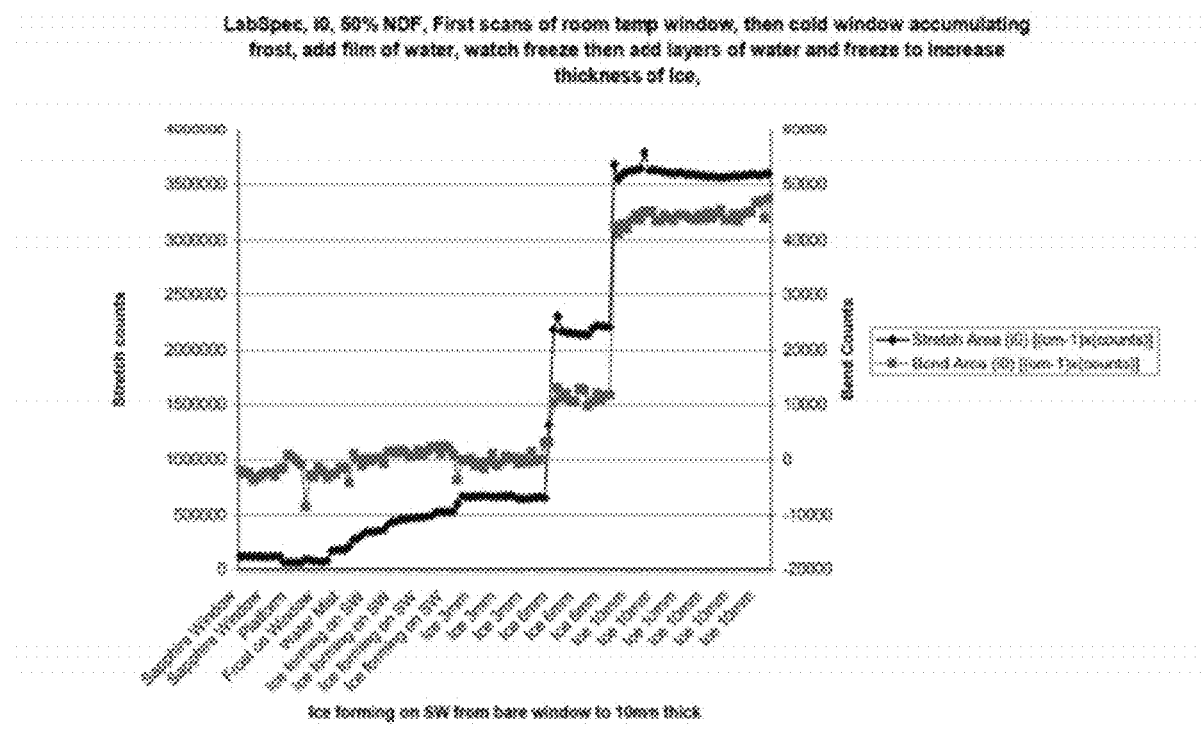
FIG. 9 shows a graph of the number of photons collected at the peaks corresponding to the ice stretching and ice bending modes before and after ice accumulated for such an open beam path embodiment showing an increase in signal with an increase in ice layer thickness. Ice layer accumulations were measured mechanically as trace amounts, 3 mm, 6 mm and 10 mm thick.
Figure 10:
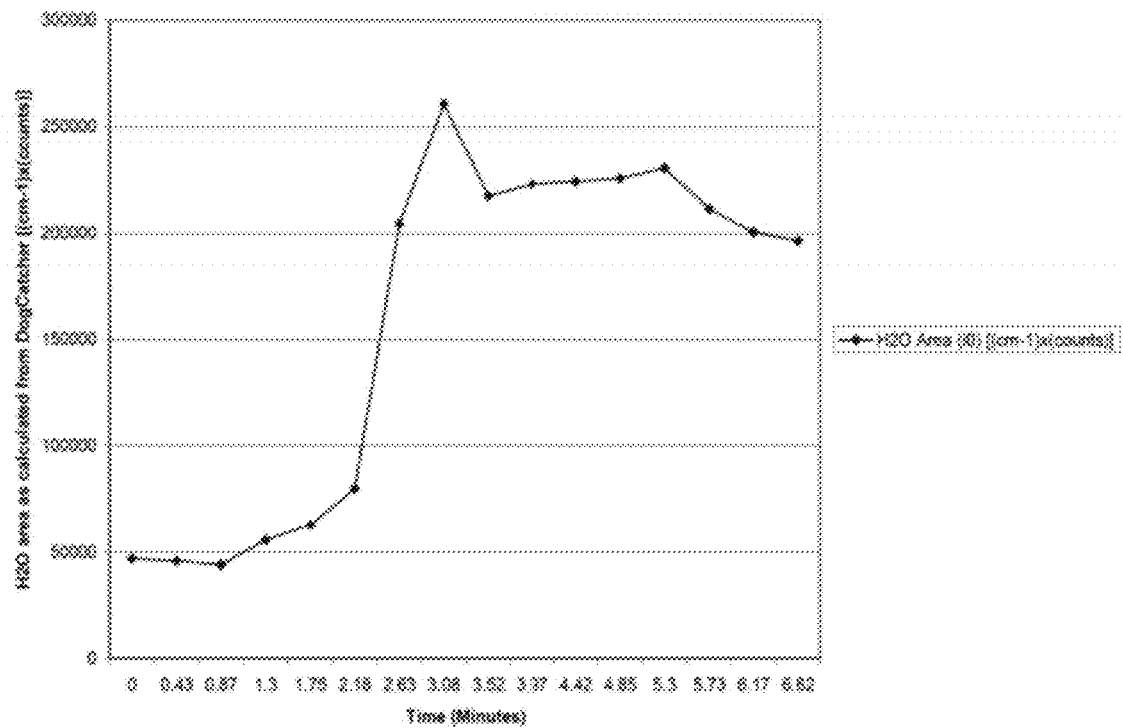
FIG. 10 shows a graph of the number of photons collected at the peak corresponding to the water bending mode as a laser was used to melt accumulated ice over time for such an open beam path embodiment showing a change in area measured as ice melts.

When ice begins to build on the surfaces, and on the window, the ice Raman scatters the excitation light and thereby changes the frequency of some of the photons in that light, the window and associated lenses collect the scattered light, and the photons signature of the Raman response of ice are then transmitted through another optical path to the sensing assembly. At the sensing assembly, the optical path is positioned so that the photons are incident on a notch filter, which is transmissive only to radiation from about 500 to about 3500 $cm^{-1}$ less than the excitation radiation frequency and the photomultiplier tube at a known time, or on a dispersive element and associated charge-coupled device sensor. The filtered signal from the ice is then read by the sensing assembly. The signal is repeatedly evaluated in order to calculate how much ice has accumulated and the rate at which ice is accumulating. Laser-induced melting of accumulated ice is accounted for when modeling the increase in ice photons collected over time. The results are transmitted to the pilots, the flight computer, and/or other entities. Other optical features are observed in order to evaluate the calibration and optical throughput of the optical path and to qualify or disqualify the Raman signals resulting from the optical path and sensing assembly. These features include the broadband signature of sunlight, the absorption signal of the optical components, the absorption signal of the protective window, and the baseline background indicating non-Raman scattering from the window, among others. After the system describes an icing event, and the aircraft returns to flight conditions under which icing does not occur, the laser continues to exit the window and heat any covering ice, thereby melting the ice and returning the window to its original configuration. In some cases, the laser power may be increased at this time in order to accelerate such melting. In cases where the window cannot be returned to a condition that provides the original optical throughput, that position can be identified for maintenance or cleaning upon landing. FIG. 8 shows spectra collected before and after onset of icing for such a system. FIG. 9 shows a graph of the number of photons collected at the ice band as ice accumulated over time for such a system. FIG. 10 shows a graph of the number of photons collected at the ice band as the laser was used to melt the accumulated ice over time for such a system. Preferably, the focusing lens or optical component can be translated using a mechanical stage or an electro-optic.

Figure 11:
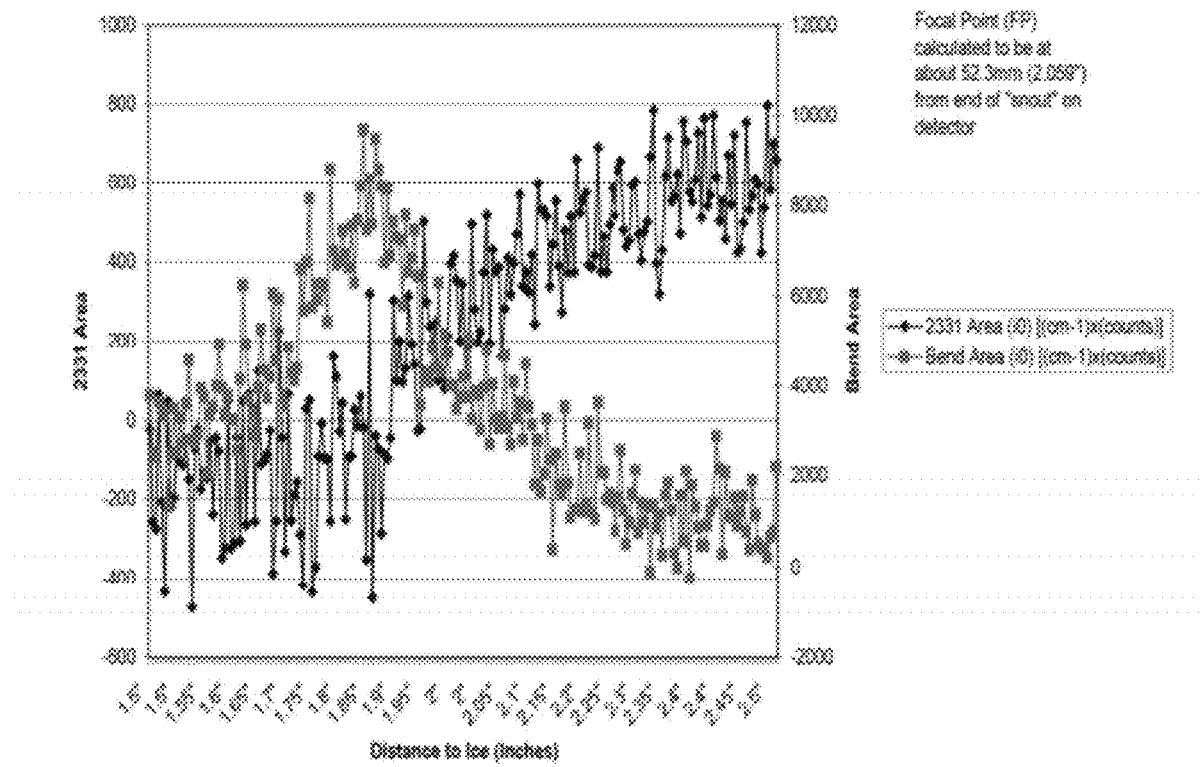
FIG. 11 shows a graph of photons collected at the frequencies corresponding to an ice bending mode and a nitrogen gas stretching mode as the focal point of an open beam path Raman spectrometer is translated across a 10 mm layer of ice formed on a sapphire window. Spectral response due to the ice bending modes is maximized when the ice layer is near the spectrometer focal point.
Figure 12:
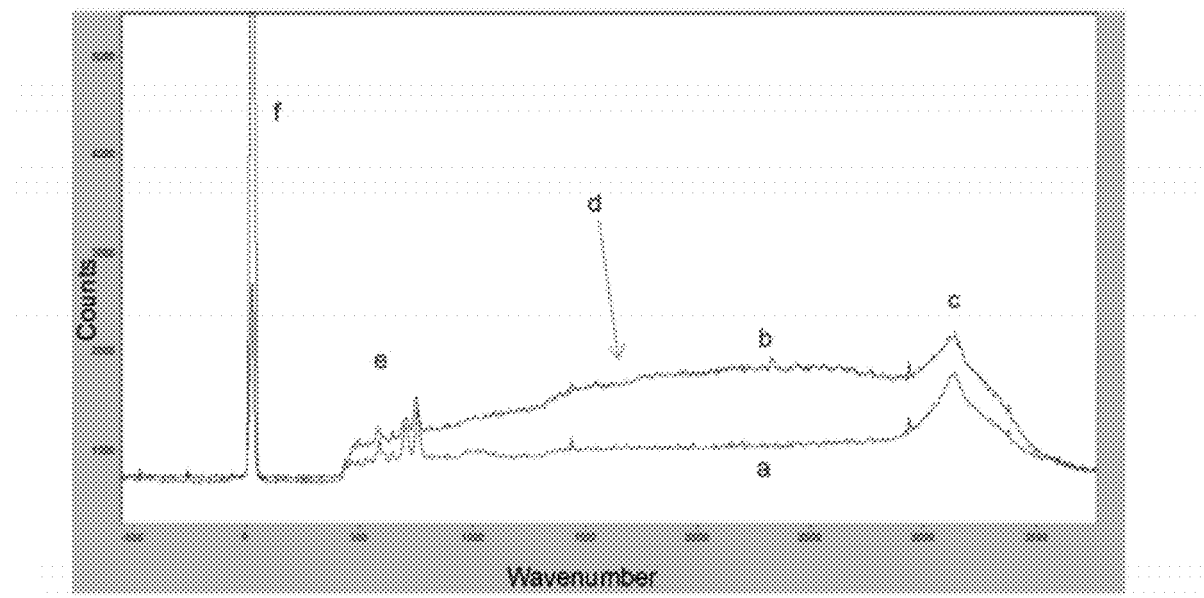
FIG. 12 shows a scan of glaze-like (a) and rime-like (b) ice, illustrating how baseline photons (at (c)) can provide a measure of backscattering, and thus opacity, and thus type of ice. The O-H stretching photons at (d) act as a measure of the thickness of the ice. The photons near (e) and (f) act as internal standards for measurement, revealing the frequency calibration and throughput of the spectrometer.
Figure 13:
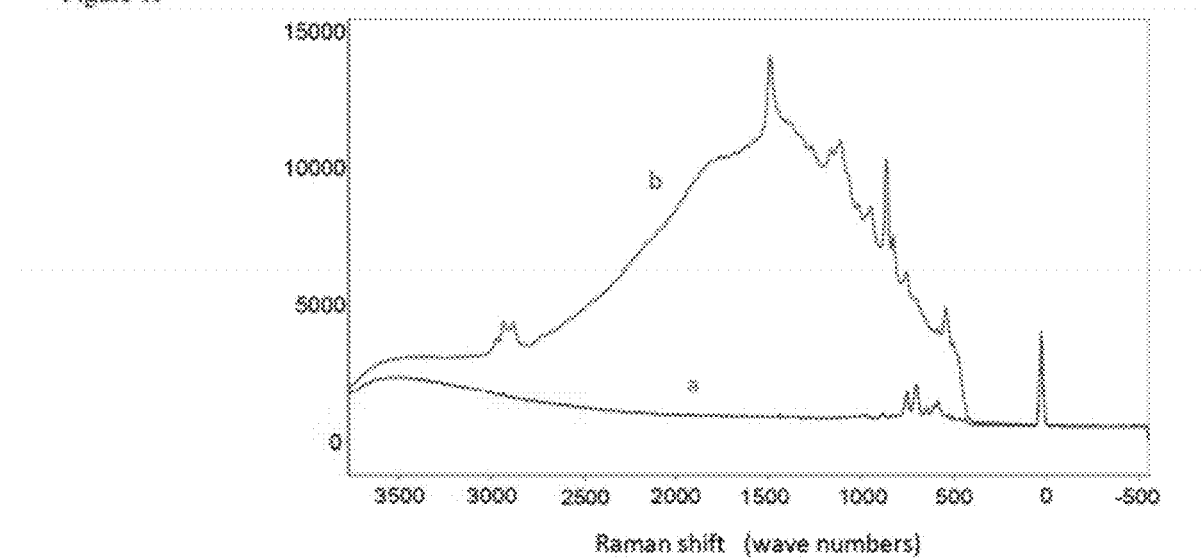
FIG. 13 shows a scan of a sapphire window before (a) and after (b) it is coated with propylene glycol, a common de-icing fluid.
Figure 14:
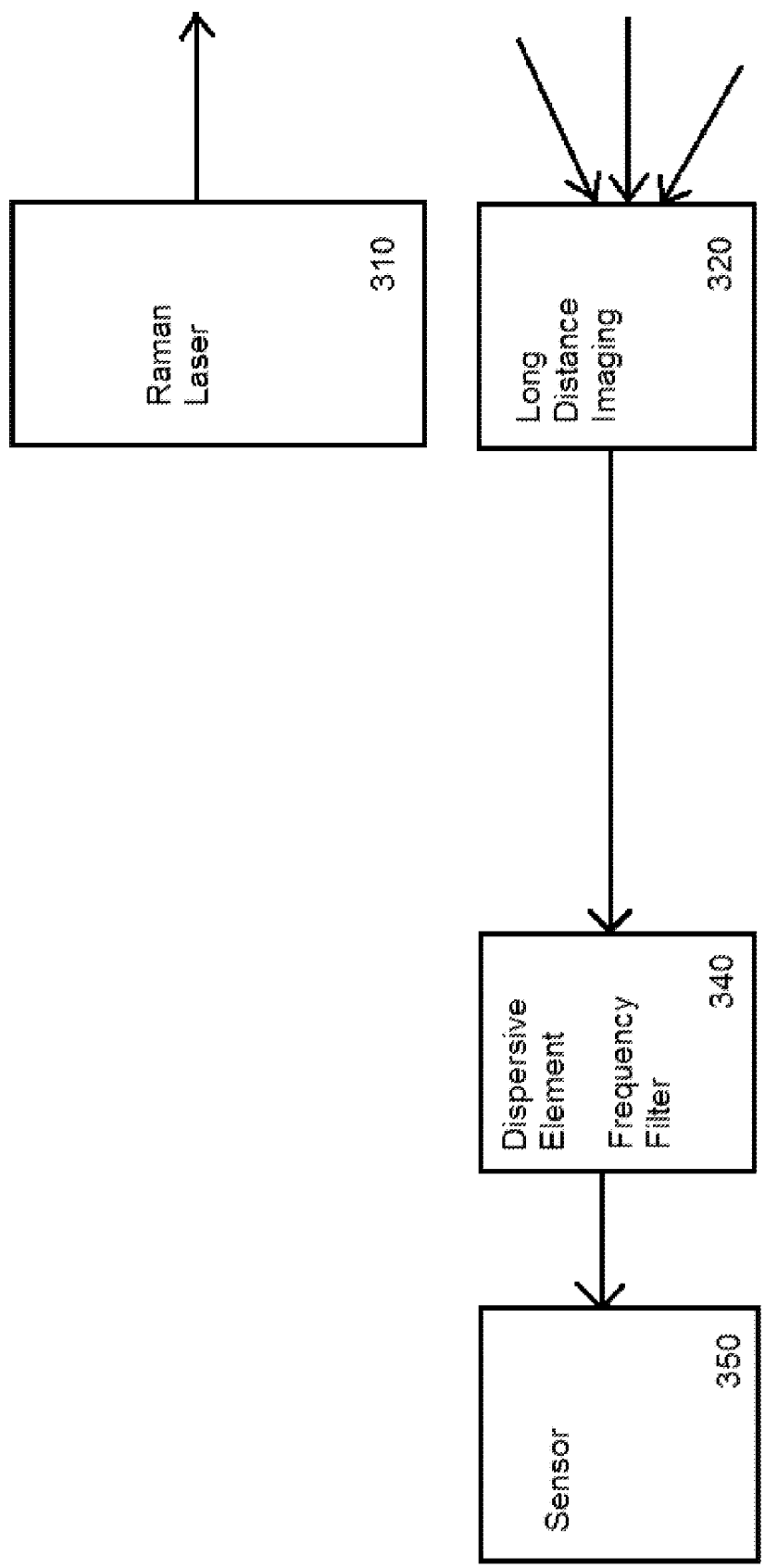
FIG. 14 shows a ground-based aircraft icing detection system comprising.

Preferably, translating the focusing lens or terminal optical component translates the focal point of the excitation radiation across any ice layer that has been accumulated. By correlating the number of photons collected to each translational position, the thickness of the accumulated ice can be measured. FIG. 11 shows a graph of photons collected at a series of translational points for a 10 mm thick accumulation of ice.

Preferably, it may be desirable to treat the tips of any fibers that are used so as to facilitate or discourage ice formation on such tips. This treatment can provide a mechanism for tuning the onset and accretion of icing on the fiber tips.

Preferably, it may be desirable to interface the fiber tips to optical components such as lenses in order to increase the throughput of the overall sensing system, or to accomplish other goals specific to the application. Likewise, treating the fiber tips or windows with optically transmissive, nanoscopically-rough layers of metals such as gold, silver or platinum can amplify the Raman signal collected through such tips and windows.

The sensing system can also be used to detect, or combined with other sensors that detect, the conditions that are favorable to icing. These conditions can include water droplet size, temperature, humidity, pressure, air or wind speed, etc.

The sensing system can also be used to detect the amount of de-icing fluid on the aircraft surfaces at a particular point in time. For example, the sensing system detects the amount of ethylene glycol or other freezing point depressant sprayed onto the aircraft prior to flight. It also identifies the point in time during the subsequent flight at which that ethylene glycol or other freezing point depressant has been removed from the aircraft surface by passing air, rain, snow, ice or other environmental conditions. Both of those calculations are used to adjust the amount of ethylene glycol or other freezing point depressant sprayed onto the plane in order to both avoid waste of the chemicals while insuring the plane has received sufficient chemicals to insure its safety.

In some cases, one sensor is used to detect the onset of icing conditions and to use another sensor assembly, such as the Raman sensing system disclosed herein, to detect the accretion of ice and the thickness of ice. For example, one sensing system is constructed from a light absorption technique and one sensing system is constructed from a Raman sensing system. The light absorption technique includes techniques such as infrared absorption, near-infrared absorption, laser absorption, and the like. The absorption technique includes the use of a spectrometer to identify absorbed light characteristic of water and ice or it includes a tunable light source, such as a diode laser that is changed in frequency to selectively excite certain chemicals such as water, carbon dioxide, and the like, and to thereby identify them. The absorption technique is used to evaluate the air surrounding an aircraft, either by direct interrogation of that air or by examination of samples of that air that have been collected, and that may have been physically or chemically manipulated. When the absorption technique indicates that the aircraft is encountering icing conditions, the Raman sensing system is then used to monitor the aircraft surfaces for accretion of ice.

The sensing system is also used to detect the different kinds of ice, such as glaze and rime ices, by interrogating their molecular, microscopic, mesoscopic and macroscopic bonding and structure, as well as detecting other optical characteristics of the ice, such as transmissivity. The system is also used to detect the conditions favorable to formation of such different ices.

In order to maintain the intensity calibration of the system, one uses an internal standard for laser output or spectrometer/fiber throughput by collecting a portion of the signal from the fibers or other optical components, or by using an optical feedback path for the laser light.

In order to maintain spectrometer stability under harsh flight conditions, it is preferable to utilize a transmissive spectrometer system instead of the more common reflective grating systems.

Preferably, a sensing system is built that detects ice formed on aircraft surfaces from outside the surfaces. Such a system is a hand-held or machine-mounted device that is used by an operator or computer to scan the aircraft surfaces for ice. The system operates by impinging a laser beam onto the aircraft surface and thereby generating scattered radiation, collecting the scattered radiation using a long focal length lens, and filtering and sensing Raman-shifted photons in the collected radiation. The system is mounted on the aircraft for use during flight, can be held in the pilot's hands for use during flight, or can be mounted at a location on the tarmac for use on the ground. In the latter (tarmac) configuration, the system is used to evaluate the presence of ice on aircraft that have recently returned from flight. Such evaluation is used to determine which aircraft have encountered icing conditions, to determine which aircraft require de-icing treatments, and the like.

In one embodiment, the hand-held system includes a 532 nm frequency doubled NdYAG laser, a 75 millimeter diameter collection lens assembly, and a Peltier-cooled charge-coupled device detector. The collection lens assembly is focused to have a focal length of from three to ten meters. The laser beam is shone onto a section of wing or engine cowling by a pilot or other operator through the aircraft window. The collection lens assembly is focused by the operator in order to maximize the laser signal collected. The collected radiation is then filtered to remove the laser signal and passed through or reflected from a dispersive element to separate the collected radiation horizontally by frequency. The dispersed radiation is impinged on the detector, and the Raman spectrum of the wing or engine cowling is thereby recorded. If the spectrum shows Raman photons at frequencies characteristic of ice, the operator can conclude that ice exists on the wing or cowling.

The light sensitive detectors described herein can be replaced with other light sensitive detectors such as avalanche photomultiplier tubes, photo transistors, PIN diodes, or other device that converts optical radiation to electronic, magnetic, physical or other signals. Similarly, the light sources described herein can be replaced with other light sources such as filtered broad band natural or unnatural light sources, light emitting diodes, gas and diode lasers, discharged lamps, and the like.

A wide range of sensitivity enhancements for Raman spectroscopy have been developed, ranging from resonance pumping of molecular energies to surface enhancement of incident light intensities to multiple-pass interactions between the incident light and the molecules of interest. Overall, then, Raman LIDAR systems that are capable of performing temperature and relative humidity measurements will require significant hardware changes in order to be relevant to the engine inlet environment. And Raman spectrometer systems that already suitable for the engine inlet environment will require enhancement of their capabilities in order to perform the measurements.

This disclosure provides optimal hardware configuration for performing relative humidity and temperature measurements in the inlet environment. Two reference points for establishing this configuration are available: current performance vs. hardware configuration for Raman LIDAR systems; and current performance vs. hardware configuration for standard Raman spectrometers.

Raman LIDAR systems typically use seven watt lasers, filtered channels, and photomultiplier tube detectors to perform measurements on water vapor and nitrogen gases located hundreds to thousands of meters away. Since the target measurement occurs only a few centimeters from the spectrometer, the amount of scattered light collected from the gas samples is much higher, relieving the need for Raman LIDAR-type high performance configurations. These optical changes are modeled using simple geometries and Raman theory. For example, the expected increase in signal intensity, between 1 km and 1 cm, is approximately 25 orders of magnitude (collected Raman signal decreases with the square of the distance to the sample). This increase in signal intensity (due, again, to the increased solid angle of scattered radiation collected by the spectrometer) enables the use of significantly lower performance lasers, filters and detectors. Likewise, standard Raman spectrometers typically use lasers with 10s to 100s of milliwatts of power, dispersive spectrometers and CCD detectors to perform measurements on liquid and solid samples. In some cases, such systems are used to perform measurements on gas samples, although trace analysis of gas is usually not performed with Raman.

We claim:

1. An aircraft icing detection system for an aircraft having a fuselage and one or a plurality of engines and wings, each having surfaces interacting with surrounding air, comprising:
   (a) a Raman sensor communicating with a computer, operator, or pilot;
   (b) a light train for transmitting incident radiation from one or more sensors integrated into aircraft surface sites to aircraft surfaces; and
   (c) a light train for returning radiation scattered from the aircraft surfaces or the surrounding air and communicating with the Raman sensor.

2. The aircraft icing detection system of claim 1, further comprising:
   (a) a plurality of input ports on the Raman sensor communicating with a computer to calculate vibrational changes at a plurality of aircraft locations; and
   (b) a plurality of fiber optic lines, each having a first and a second end, wherein the first end optically communicates with an input port of a Raman sensor, and the second end is integrated into an aircraft surface.

3. The aircraft icing detection system of claim 2, wherein the Raman sensor and computer calculate vibrational changes at a plurality of aircraft locations.

4. The aircraft icing detection system of claim 2, wherein the Raman spectrometer is located in the fuselage of the aircraft.

5. The aircraft icing detection system of claim 2, wherein there are at least twenty fiber optic lines, each leading to various positions on the aircraft that tend to ice, including, but not limited to, forward wing edges, air speed sensors, and the engine inlets, or to samples of surrounding air.

6. A ground-based aircraft icing detection system comprising:
   (a) a ground based laser capable of pointing onto specific sites of a passing aircraft;
   (b) a ground based long-distance imaging system capable of collecting light scattered from the specific sites and transmitting said light to a light detector; and
   (c) a light detector device that uses dispersive elements or frequency filters to isolate photons characteristic of ice and focus those photons onto a sensor.

7. The ground-based aircraft icing detection system of claim 6, wherein the light detector device is selected from the group consisting of a Raman spectrophotometer, a photomultiplier tube or plurality thereof, a PIN diode, avalanche photomultiplier tubes, photo transistors, charge coupled device, and combinations thereof.

8. A process for detecting a molecular monolayer or greater amounts of ice formed on an aircraft surface, comprising:
   (a) providing an aircraft with a Raman sensor located in the fuselage having a plurality of input ports and communicating with a computer to calculate vibrational changes, and a plurality of fiber optic lines, each having a first and a second end, wherein the first end optically communicates with an input port of a Raman sensor, and the second end is focused on a structure located on a wing surface or an engine surface; and (b) reading each fiber optic line to detect ice formed on the surface.

9. The process for detecting a molecular monolayer or greater amounts of ice formed on an aircraft surface of claim 8, wherein the Raman spectrometer focuses an exciting laser beam onto the surface of the structure of interest, the scattered light is collected and filtered, and photons related to the Raman signature of ice are detected.

10. A process for detecting a molecular monolayer or greater amounts of ice formed on an aircraft surface, comprising:

(a) providing an aircraft with a Raman sensor located in the fuselage having a plurality of input ports and communicating with a computer to calculate vibrational changes, and a plurality of fiber optic lines, each having a first and a second end, wherein the first end optically communicates with an input port of a Raman sensor, and the second end is focused on a structure located on a wing surface or an engine surface;

(b) reading each fiber optic line to detect ice formed on the surface (c) providing a lens assembly capable of translating a focal point of a Raman spectrometer;

(d) scanning said focal point through a layer of ice;

(e) calculating the Raman signal of ice as a function of translation point in order to identify the beginning and ending positions of the ice; and (f) calculating the thickness of the ice using the beginning and ending positions of the ice.

11. The process for detecting a molecular monolayer or greater amounts of ice formed on an aircraft surface of claim 10, wherein the focal point is moved by physically adjusting the position of the lens assembly relative to the position of the layer of ice.

12. The process for detecting a molecular monolayer or greater amounts of ice formed on an aircraft surface of claim 10, wherein the focal point is moved by electronically adjusting the focal length of the lens assembly relative to the position of the layer of ice.

13. The process for detecting a molecular monolayer or greater amounts or ice formed on an aircraft surface of claim 12, wherein the depth of field is increased by increasing the F-stop or decreasing a magnification within a lens assembly.

14. The process for detecting a molecular monolayer or greater amounts of ice formed on an aircraft surface of claim 12, wherein the process further comprises calculating ice thickness by determining height of ice signal in a Raman spectrometer in view of the depth of field of the signal.

15. The process for detecting a molecular monolayer or greater amounts of ice formed on an aircraft surface of claim 11, wherein the process further comprises irradiating the aircraft surface where ice was detected with laser or other light source in order to melt the ice.

16. A process for determining ice thickness on an aircraft having surfaces, comprising:

(a) providing a Raman spectrometer optical detection device having a fixed focal point and communicating with a computer to calculate vibrational changes of molecules on the aircraft surface;

(b) providing a plurality of sensors in optical communication with the Raman spectrometer wherein a first group of sensors are placed at one position relative to aircraft surfaces prone to icing to detect the presence of ice and a second group of sensors are placed at different positions on aircraft surfaces prone to icing;

(c) transmitting an exiting laser beam from the Raman spectrometer onto the aircraft surface, the scattered light is collected by the sensors and filtered and photons related to a Raman signature for ice are detected; and (d) using the computer to correlate correlating the optical sensor data from the first group and second group of sensors to determine presence and thickness of ice at the location of each sensor.

17. The process for determining ice thickness on an aircraft having surfaces of claim 16, wherein the process further comprises irradiating the aircraft surface where ice was detected with a laser or other light source to melt the ice.

18. The process for determining ice thickness on an aircraft having surfaces of claim 17, wherein the process further comprises directing the light to an aircraft surface to melt any ice formed on its outer surface.

19. The process for determining ice thickness on an aircraft having surfaces of claim 16, wherein the second group of sensors is placed orthogonal to aircraft surfaces prone to icing.

20. The aircraft icing detection system of claim 5 further comprising a window integrated into aircraft surface using a mechanical translation stage that allows a focal point of an optically transparent tip to be moved to five millimeters outside the window to sample the aircraft surface or surrounding air.

* * * * *